(12) United States Patent
Padi et al.

(10) Patent No.: US 7,659,406 B2
(45) Date of Patent: Feb. 9, 2010

(54) PROCESS FOR PREPARING VALSARTAN

(75) Inventors: Pratap Reddy Padi, Hyderabad (IN); Satya Narayana Bollikonda, Hyderabad (IN); Ananda Mohan Jasty, Hyderabad (IN); Suma Latha Yasareni, Khammam (IN); Vishal Dayaram Parmar, Ahmednagar (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 514 days.

(21) Appl. No.: 11/324,979

(22) Filed: Jan. 3, 2006

(65) Prior Publication Data

US 2006/0149079 A1 Jul. 6, 2006

Related U.S. Application Data

(60) Provisional application No. 60/641,097, filed on Jan. 3, 2005.

(51) Int. Cl.
*C07D 257/04* (2006.01)
(52) U.S. Cl. ...................... 548/253
(58) Field of Classification Search .............. 548/253
See application file for complete search history.

(56) References Cited

U.S. PATENT DOCUMENTS 5,399,578 A * 3/1995 Buhlmayer et al. ......... 514/381

FOREIGN PATENT DOCUMENTS

WO   WO 2004/111018   * 12/2004

* cited by examiner

*Primary Examiner*—Golam M. M. Shameem
*Assistant Examiner*—Susannah Chung
(74) *Attorney, Agent, or Firm*—Robert A. Franks; Lee Banks; Anjum Swaroop

(57) ABSTRACT

A process for preparing valsartan.

16 Claims, No Drawings

PROCESS FOR PREPARING VALSARTAN

CROSS-REFERENCE TO RELATED APPLICATION

This application is a nonprovisional filing of U.S. Provisional Application No. 60/641,097 filed on Jan. 3, 2005, the entire content of which is hereby incorporated by reference.

INTRODUCTION TO THE INVENTION

The present invention relates to an improved process for the preparation of valsartan and its pharmaceutically acceptable salts.

Valsartan is chemically known as N-(1-oxopentyl)-N-[[2'-(1H-tetrazol-5-yl) [1,1'-biphenyl]-4-yl]methyl]-L-valine and can be represented structurally by Formula I.

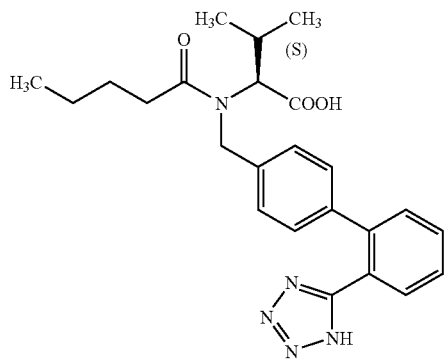

Valsartan is a non-peptide, orally active, specific angiotensin II antagonist, useful in the treatment of hypertension and is commercially available in the market under the brand name DIOVAN™ as 40, 80, 160 and 320 mg tablets.

U.S. Pat. No. 5,399,578 discloses valsartan, its pharmaceutically acceptable salts, pharmaceutical compositions comprising valsartan and their use in treating high blood pressure and cardiac insufficiency. It also discloses a process for the preparation of valsartan, which can be depicted by Scheme 1.

Scheme 1

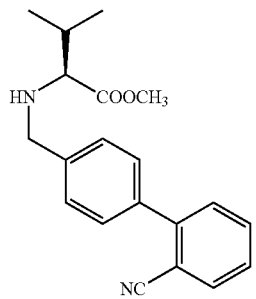

Formula II

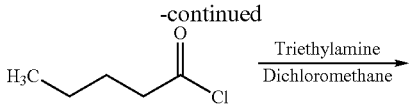

Formula III

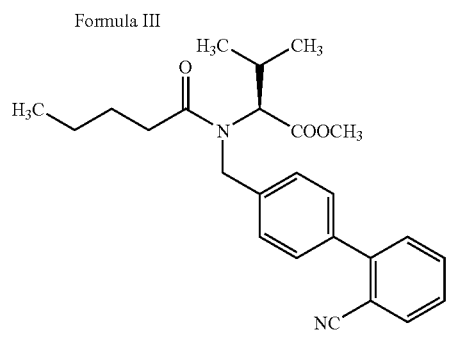

Briefly, the process for the preparation of valsartan comprises of the condensation of N-[(2'-cyanobiphenyl-4-yl)methyl]-(L)-valine methyl ester of Formula II with valeryl chloride of Formula III in the presence of triethylamine and dichloromethane, followed by flash chromatography, to give the compound N-[(2'-cyanobiphenyl-4-yl)methyl]-N-valeryl-(L)-valine methyl ester of Formula IV. The compound of Formula IV on tetrazole formation using tributyltin azide and subsequent hydrolysis using sodium hydroxide, followed by flash chromatography, gives valsartan of Formula I.

The aforementioned process uses triethylamine in the process for the preparation of the compound of Formula IV, in which process the reaction is incomplete due to presence of moisture, affecting the quality of the product, leading to a lower yield and requiring flash chromatography for purification. Conversion of the compound of Formula IV to valsartan also involves flash chromatography, which makes the process difficult to operate on an industrial scale.

Consequently, there is a long-felt need for a process for the preparation of valsartan which not only overcomes the problems in the art processes as mentioned above, but is also safe, cost effective, and industrially feasible.

SUMMARY OF THE INVENTION

The present invention relates to an improved process for the preparation of valsartan of Formula I, and pharmaceutically acceptable salts thereof, one embodiment of the process comprising the steps of:

a) condensation of N-[(2'-cyanobiphenyl-4-yl)methyl]-(L)-valine methyl ester compound of Formula II or its hydrochloride salt with the valeryl chloride compound of Formula III in the presence of an inorganic base and a suitable solvent to give the (N-[(2'-cyanobiphenyl-4-yl)methyl]-N-valeryl-(L)-valine methyl ester compound of Formula IV;

b) tetrazole formation of (N-[(2'-cyanobiphenyl-4-yl)methyl]-N-valeryl-(L)-valine methyl ester compound of Formula IV in the presence of suitable reagents and suitable solvents to provide an intermediate compound of Formula V;

c) hydrolysis of the compound of Formula V using a suitable base in the presence of a suitable solvent to yield valsartan; and d) optionally, recrystallisation of the valsartan of step (c) in a suitable solvent(s) to provide the purified valsartan of Formula I.

An aspect of the invention comprises a process for preparing valsartan, comprising condensing N-[(2'-cyanobiphenyl-4-yl)methyl]-(L)-valine methyl ester, or a salt thereof, with valeryl chloride in the presence of an inorganic base to form N-[(2'-cyanobiphenyl-4-yl)methyl]-N-valeryl-(L)-valine methyl ester.

A further aspect of the invention comprises a process for preparing valsartan, comprising hydrolyzing a compound having the formula

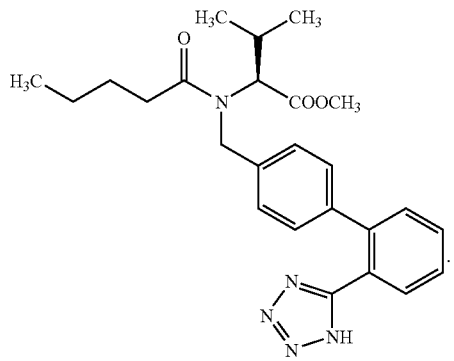

An additional aspect of the invention comprises a compound having the formula

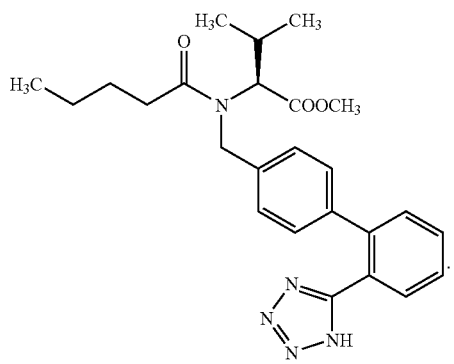

DETAILED DESCRIPTION

The present invention relates to an improved process for the preparation of valsartan of Formula I, and pharmaceutically acceptable salts thereof, comprising the steps of:

a) condensation of N-[(2'-cyanobiphenyl-4-yl)methyl]-(L)-valine methyl ester compound of Formula II or a salt thereof

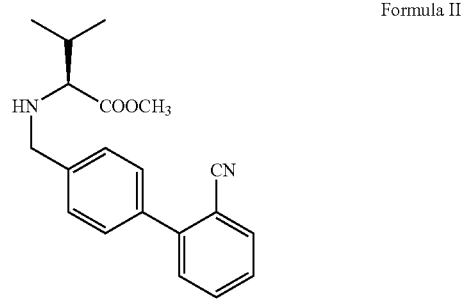

Formula II with the valeryl chloride compound of Formula III

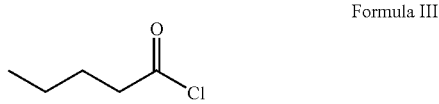

Formula III in the presence of an inorganic base and a suitable solvent to provide (N-[(2'-cyanobiphenyl-4-yl)-methyl]-N-valeryl-(L)-valine methyl ester of Formula IV;

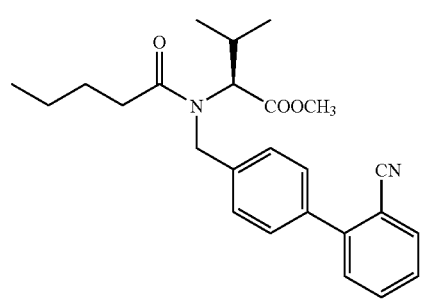

Formula IV b) tetrazole formation of the N-[(2'-cyanobiphenyl-4-yl)methyl]-N-valeryl-(L)-valine methyl ester compound of Formula IV in the presence of suitable reagents and suitable solvents, to give an intermediate compound of Formula V;

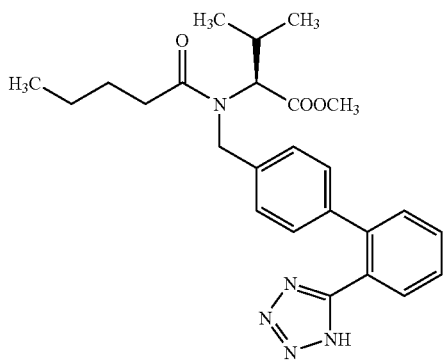

Formula V c) hydrolysis of the intermediate compound of Formula V using a suitable base in the presence of a suitable solvent to provide valsartan of Formula I; and d) optionally, recrystallization of crude valsartan in a suitable solvent(s) to give purified valsartan of Formula I.

Step a) involves condensation of N-[(2'-cyanobiphenyl-4-yl)-methyl]-(L)-valine methyl ester or a salt, such as its hydrochloride salt, with valeryl chloride in the presence of an inorganic base and a suitable solvent to give (N-[(2'-cyano-biphenyl-4-yl)methyl]-N-valeryl-(L)-valine methyl ester.

Suitable inorganic bases that can be used in step a) include but are not limited to: hydroxides of alkali metals such as lithium hydroxide, sodium hydroxide, potassium hydroxide, and the like; carbonates of alkali metals such as sodium carbonate, potassium carbonate, and the like; and bicarbonates of alkali metals such as sodium bicarbonate, potassium bicarbonate, and the like; or mixtures thereof.

The amount of base that can be used in the reaction can vary depending upon the base used. Suitably, the molar ratio of base to the starting material compound of Formula II can range from about 3 to 6, or about 4 to 5, or about 4.5.

Suitable solvents that can be used include but are not limited to: ketones such as acetone, ethyl methyl ketone, methyl isobutyl ketone and the like; esters such as ethyl acetate, n-propyl acetate, isopropyl acetate, n-butyl acetate, and the like; nitrites such as acetonitrile, propionitrile and the like; hydrocarbons such as toluene, xylene and the like; halogenated hydrocarbons such as dichloromethane, chloroform and the like; aprotic polar solvents such as N,N-dimethylformamide (DMF), dimethylsulfoxide (DMSO), N,N-dimethylacetamide (DMA) and the like; and water; or mixtures thereof in various proportions.

Suitable temperatures for conducting the reaction can range from about −15° C. to 50° C., or about 25° C. to 35° C., or about 0° C. to 5° C.

Step b) involves tetrazole formation of the compound of Formula IV in the presence of a suitable tetrazole forming reagents and suitable solvent to give an intermediate compound of Formula V.

Suitable tetrazole formation reagents include but are not limited to tributyltin azide and the like, which may be prepared insitu by the reaction of tributyltin chloride and sodium azide.

Suitable solvents that can be used in the tetrazole formation reaction include any solvent or mixture of solvents. Examples include, without limitation thereto ketones such as acetone, ethyl methyl ketone, methyl isobutyl ketone and the like; esters such as ethyl acetate, n-propyl acetate, isopropyl acetate, n-butyl acetate, and the like; halogenated hydrocarbons such as, dichloromethane, chloroform and the like; and aromatic hydrocarbons such as benzene, toluene, xylene and the like.

Suitable temperatures for the tetrazole formation reaction can range from about 0° C. to 120° C., or about 50° C. to 100° C., or at the reflux temperature of the solvent used.

The intermediate tetrazole compound of Formula V thus formed may or may not be isolated and can be converted into corresponding acid in step c).

Step c) involves hydrolyzing the intermediate compound of Formula V using a suitable base in presence of a suitable solvent to provide crude valsartan of Formula I Suitable inorganic bases that can be used in step c) include but are not limited to: hydroxides of alkali metals such as lithium hydroxide, sodium hydroxide, potassium hydroxide, and the like; carbonates of alkali metals such as sodium carbonate, potassium carbonate, and the like; bicarbonates of alkali metals such as sodium bicarbonate, potassium bicarbonate, and the like; or mixtures thereof.

In one embodiment these bases can be used as their solutions in suitable solvents.

Suitable solvents that can be used in the hydrolysis of the tetrazole intermediate compound include any solvent or mixture of solvents in which the required components are soluble. Examples include alcohols such as methanol, ethanol, propanol and the like; ketonic solvents such as acetone, ethyl methyl ketone, methyl isobutyl ketone and the like; esters such as ethyl acetate, n-propyl acetate, isopropyl acetate, n-butyl acetate, and the like; halogenated solvents such as, dichloromethane, chloroform and the like; aromatic hydrocarbons such as benzene, toluene, xylene and water.

Step d) involves crystallization by dissolving crude valsartan in a suitable solvent to form a clear solution and then cooling to give a pure valsartan compound of Formula I. For obtaining high product yield, the solute concentration should be high, and frequently elevated temperatures will be required to dissolve sufficient solute.

Suitable solvents that can be used in step d) include any solvent or mixture of solvents in which the required components are soluble. Examples include without limitation: ketones such as acetone, ethyl methyl ketone, methyl isobutyl ketone and the like; esters such as methyl acetate, ethyl acetate, n-propyl acetate, isopropyl acetate, n-butyl acetate, and the like; halogenated solvents such as, dichloromethane, chloroform and the like; nitriles such as acetonitrile, propionitrile and the like;

Suitable temperatures for dissolving crude valsartan in solvent to form clear solution can range from about 0-120° C., or about 50-100° C., or at the reflux temperature of the solvent used.

In one embodiment, clear solution thus obtained during the process can optionally be treated with activated charcoal or any other adsorbent material to improve the color of the compound.

Suitable temperatures for solid separation can range from about −20 to 50° C., about −10 to 10° C., about 0 to 5° C., or any other temperature below the solute dissolution temperature.

Isolation of the solid can be carried out by using conventional techniques such as centrifugation, decantation, gravity filtration, vacuum filtration, or other techniques known in the art for the separation of solids.

A solid product can be dried using any technique, such as for example fluidized bed drying, aerial drying, oven drying, or other techniques known in the art. Drying can be conducted at temperatures of about 20-100° C. or about 60-70° C. with or without an application of vacuum. It is also conceived that the drying could be carried out under an inert atmosphere, if desired.

Valsartan prepared according to the process of the present invention can be converted into its pharmaceutically acceptable salts by using methods such as those described in U.S. Patent Application Publication No. 2005/0101652.

The process of the present invention is improved, cost-effective, eco-friendly and reproducible on an industrial scale.

Certain aspects and embodiments of the processes described herein are further described in the following examples. These examples are provided solely for the purpose of illustrating certain aspects and embodiments of the invention and therefore should not be construed as limiting the scope of the invention. Purity information in the examples was determined using high performance liquid chromatography ("HPLC") analysis.

EXAMPLE 1

Preparation of N-[(2'-CYANOBIPHENYL-4-YL)-METHYL]-N-VALERYL-(L)-VALINE Methyl Ester (Formula IV)

150 g N-[(2'-cyanobiphenyl-4-yl)methyl]-(L)-valine methyl ester hydrochloride was charged into a round bottomed flask containing a mixture of sodium bicarbonate (158.1 g), water (450 ml) and toluene (900 ml). The contents were stirred at 28° C. for 25 minutes and then cooled to 0° C. 110.9 g of valeryl chloride was added slowly to the reaction mass at 0-20° C. over about 55 minutes. The reaction mass was stirred at about 2-4° C. for about 2 hours. Reaction completion was confirmed by thin layer chromatography and the reaction mixture was allowed to attain 28° C. 450 ml of water was added to the reaction mass and stirred for about 20 minutes. The organic layer was separated, washed with a solution of sodium bicarbonate (30 g) in water (450 ml) twice, followed by washing with water (450 ml). The organic layer was concentrated under reduced pressure at 60-68° C. to obtain 183 g of the title compound.

(Purity by HPLC 98.9 area-%)

EXAMPLE 2

Preparation of N-(1-OXOPENTYL)-N-[[2'-(1H-TETRAZOL-5-YL) [1,1'-BIPHENYL]-4-YL]ME-THYL]-L-VALINE (Valsartan)

A mixture of o-xylene (510 ml), N-[(2'-cyanobiphenyl-4-yl)-methyl]-N-valeryl-(L)-valine methyl ester (169.8 g), tributyl tin chloride (204.2 g) and sodium azide (54.4 g) was charged into a round bottomed flask and heated to reflux. The reaction mixture was maintained at reflux for about 40 hours and then cooled to 30° C. 70.2 g of lithium hydroxide in water (1190 ml) was added to the reaction mass at 30° C. and stirred for 13 hours. The aqueous layer was separated and washed twice with toluene (2×170 ml). To the separated aqueous layer 170 ml of dichloromethane was added and the pH was adjusted to 6.75 using 20% aqueous acetic acid (205 ml). The aqueous layer was separated and washed with dichloromethane (170 ml). To the separated aqueous layer dichloromethane (680 ml) was added and the pH was further adjusted to 5, using acetic acid (48 ml). The aqueous layer was separated and extracted with dichloromethane (680 ml). The combined organic layer was washed with water (680 ml), followed by washing with a solution of sodium chloride (34 g) in water (680 ml). The organic layer was concentrated at atmospheric pressure and about 90% of the solvent was distilled off at 40-48° C. To the residual mass cyclohexane (340 ml) was added and concentrated under reduced pressure at 50-58° C. to obtain a residue. The residue was cooled to 30° C., then 680 ml of cyclohexane was added to the residue and stirred for about 50 minutes at 28-30° C. The resultant solid was filtered and washed with cyclohexane (170 ml). The obtained solid was dried at about 50° C. to give 118.2 g of the solid product. (Purity by HPLC 96.6 area-%)

A mixture of above obtained solid (110 g) and dichloromethane (1100 ml) was charged into a flask and refluxed for 15 minutes to produce a clear solution. To the reaction mass 11 g of activated charcoal was added and maintained at reflux for 25 minutes. The mass was filtered hot through a flux calcined diatomaceous earth (Hyflow) bed, and washed with dichloromethane (55 ml). The filtrate was cooled to 5° C. and stirred for 35 minutes for isolation of the solid. The solid was filtered and washed with dichloromethane (55 ml). The obtained solid was dried at 50-52° C. for about 6 hours to yield 65.2 g of the title compound. (Purity by HPLC 98.99 area-%)

EXAMPLE 3

Alternate Process for the Preparation of N-(1-OXO-PENTYL)-N-[[2'-(1H-TETRAZOL-5-YL) [1,1'-BIPHENYL]-4-YL]METHYL]-L-VALINE (Valsartan)

A mixture of water (42.5 ml) and sodium azide (15.8 g) was charged into a round bottom flask and cooled to about 8° C. To the mixture tributyl tin chloride (79.4 g) was added and maintained at 5-80° C. for about 1 hour 15 minutes. The resulting tributyl tin azide was extracted into dichloromethane (85 ml). The organic layer was washed with water (85 ml) and dried over sodium sulfate.

To the resultant tributyl tin azide solution in methylene chloride, N-[(2'-cyanobiphenyl-4-yl)-methyl]-N-valeryl-(L)-valine methyl ester (28.3 g) and o-xylene (85 ml) were added and heated to reflux. The reaction mass was maintained at reflux for about 6 hours, 15 minutes and then cooled to about 30° C. 11.7 g of lithium hydroxide in water (198 ml) was added and stirred for about 10 hours at 28-30° C. Reaction completion was confirmed by thin layer chromatography and the organic and aqueous layers were separated. The aqueous layer was washed twice with toluene (2×28.3 ml). To the aqueous layer was added dichloromethane (28.3 ml) and the pH was adjusted to 6.7 using a 20% aqueous acetic acid (32 ml) solution. The aqueous layer was separated and washed with dichloromethane (28.3 ml). The aqueous layer was separated and 113.2 ml of dichloromethane was added. The pH of the reaction mass was adjusted to 5 using acetic acid (8.2 ml). The reaction mixture was stirred for 15 minutes and the organic and aqueous layers were separated. The aqueous layer was again extracted with dichloromethane (113.2 ml). The combined organic layers were washed with water (113.2 ml) and then with a solution of sodium chloride (5.7 g) in water (113.2 ml) followed by a further wash with water (113.2 ml). The organic layer was concentrated at atmospheric pressure and about 90% of the solvent was distilled off at 42° C. To the residual mass cyclohexane (56.6 ml) was added and concentrated under reduced pressure at about 55° C. to obtain a residue. The residue was cooled to 30° C.; 113.2 ml of cyclohexane was added to the residue and stirred for about 55 minutes at 28-30° C. The resultant solid was filtered and washed with cyclohexane (28.3 ml). The obtained solid was dried at about 50° C. for about 6 hours to give 22.3 g of the crude valsartan. (Purity by HPLC 98.75 area-%)

EXAMPLE 4

Purification of Valsartan 55 g of crude valsartan prepared according to Example 2 was charged into a round bottomed flask containing ethyl acetate (330 ml) and the contents were heated to reflux under stirring to form a clear solution. To the clear solution, 5.5 g of activated charcoal was added and stirred at reflux for about 35 minutes. The reaction mass was filtered hot through a flux calcined diatomaceous earth (Hyflow) bed and the bed was washed with ethyl acetate (27.5 ml). The resultant filtrate was cooled to about 35° C. and seeded with 2.75 g of pure valsartan. The seeded solution was stirred for 1 hour, 15 minutes at 35° C. and subsequently cooled stepwise: to 30° C. for 1 hour, 15 minutes; further to 15° C. for about 40 minutes; and further to about 5° C. for about 2 hours, 20 minutes; all accompanied by stirring. The separated solid was filtered and washed with ethyl acetate (27.5 ml) to get the wet solid compound.

The wet solid was dried under a reduced pressure of about 700 mm Hg using a cone vacuum drier at 30° C. for about 3 hours. It was then further dried at 50-52° C. for about 4 hours in the cone drier followed by sieving through a 40-mesh sieve. The resultant partially dried material was kept in a vacuum oven and dried at about 70° C. for about 24 hours to afford 39.3 g of the title compound. (Purity by HPLC: 99.86 area-%)

EXAMPLE 5

Commercial Scale Drying of Valsartan 9.5 kg of wet valsartan solid prepared similarly to Example 4 was charged into a cone vacuum drier and dried under reduced pressure of about 650-670 mm Hg at about 30° C. for about 4 hours and subjected to multi milling using a 40 mesh screen at 30° C. The milled material was then dried at 42-44° C. for about 2 hours, 15 minutes using a fluid bed drier. The temperature was increased to 52° C. and the material was dried at 52-54° C. for about 3 hours, 15 minutes using a fluid bed drier to afford 5.58 kg of the partially dried material. 2.8 kg of the resultant partially dried material was subjected to air jet milling at an air pressures of 3.0-3.9 kg/cm² at room temperature. The material thus obtained was finally dried at 62-69° C. for about 14 hours using a fluid bed drier (until loss on drying was less than 0.5% w/w) and sieved through a 40 mesh sieve yielding 2.2 kg of the pure valsartan.

EXAMPLE 6

Preparation of the Compound of Formula V 50 g of valsartan was charged into a round-bottomed flask containing a mixture of 500 ml of methanol and 15 ml of thionyl chloride at 4-5° C. The mixture was allowed to attain room temperature and was stirred for 3 hours. Solvent was distilled from the reaction mass below 40° C. and the residue was cooled to about 20° C. 250 ml of water was added to the residue and extracted with dichloromethane (3×200 ml). The organic layer was washed with 20% sodium chloride solution (250 ml). The organic layer was dried over sodium sulfate and solvent was distilled completely to get 46 g of the title compound as a solid ¹H NMR (200 MHz, CDCl₃, δ in ppm): 0.8-1.1 (m, 9H), 1.2-1.8 (m, 4H), 2.2-2.7 (m, 3H), 3.4-3.6 (s, 3H), 4.0-5.0 (m, 3H), 7.1-8.2 (m, 8H).

Mass: m/z 450.

What is claimed is:

1. A process for preparing valsartan, comprising condensing N-[(2'-cyanobiphenyl-4-yl)methyl]-(L)-valine methyl ester, or a salt thereof, with valeryl chloride in the presence of a reaction medium consisting essentially of an inorganic base and at least one solvent, to form N-[(2'-cyanobiphenyl-4-yl)methyl]-N-valeryl-(L)-valine methyl ester.

2. The process of claim 1, wherein an inorganic base comprises at least one alkali metal hydroxide, carbonate, or bicarbonate.

3. The process of claim 1, wherein a molar ratio of inorganic base to N-[(2'-cyanobiphenyl-4-yl)methyl]-(L)-valine methyl ester is between about 3 and about 6.

4. The process of claim 1, wherein a molar ratio of inorganic base to N-[(2'-cyanobiphenyl-4-yl)methyl]-(L)-valine methyl ester is between about 4 and about 5.

5. The process of claim 1, further comprising reacting N-[(2'-cyanobiphenyl-4-yl)methyl]-N-valeryl-(L)-valine methyl ester with a tetrazole forming reagent, to form a compound having the formula

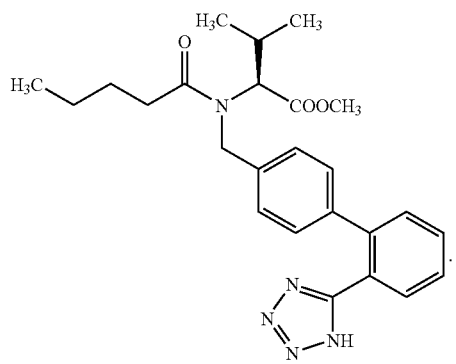

6. The process of claim 5, wherein a tetrazole forming reagent comprises tributyltin azide.

7. The process of claim 5, further comprising hydrolyzing a compound having the formula

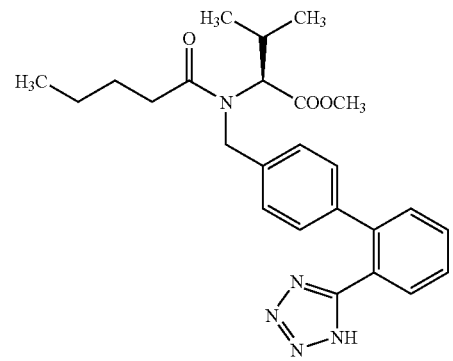

to form valsartan.

8. The process of claim 7, wherein hydrolyzing comprises reacting with a base.

9. The process of claim 7, wherein hydrolyzing comprises reacting with at least one alkali metal hydroxide, carbonate, or bicarbonate.

10. The process of claim 7, further comprising purifying valsartan by crystallization from a ketone, ester, halogenated solvent, or nitrile.

11. The process of claim 1, wherein an inorganic base comprises at least one of lithium hydroxide, sodium hydroxide, and potassium hydroxide.

12. The process of claim 1, wherein an inorganic base comprises at least one of sodium carbonate and potassium carbonate.

13. The process of claim 1, wherein an inorganic base comprises at least one of sodium bicarbonate and potassium bicarbonate.

14. The process of claim 1, wherein a solvent comprises a ketone, an ester, a nitrile, a hydrocarbon, a halogenated hydrocarbon, an aprotic polar solvent, water, or a mixture of two or more thereof.

15. The process of claim 1, wherein a solvent comprises toluene, a xylene, or a mixture thereof.

16. The process of claim 1, wherein condensing occurs at about −15° C. to about 50° C.

* * * * *